United States Patent
Li et al.

(10) Patent No.: US 7,621,169 B2
(45) Date of Patent: Nov. 24, 2009

(54) SYSTEMS AND METHODS FOR INTEGRATING A NAVIGATION FIELD REPLACEABLE UNIT INTO A FLUOROSCOPY SYSTEM

(75) Inventors: Dun Alex Li, Salem, NH (US); Mohamed Ali Hamadeh, Kingston, NH (US); Daniel A. Beaudet, Dover, NH (US); Lisa Marie Last, Wakefield, MA (US)

(73) Assignee: General Electric Company, Schenectady, NY (US)

( * ) Notice: Subject to any disclaimer, the term of this patent is extended or adjusted under 35 U.S.C. 154(b) by 429 days.

(21) Appl. No.: 11/553,291

(22) Filed: Oct. 26, 2006

(65) Prior Publication Data
US 2008/0161684 A1 Jul. 3, 2008

(51) Int. Cl.
*G01D 18/00* (2006.01)
(52) U.S. Cl. ....................................................... 73/1.01
(58) Field of Classification Search ................... 378/91, 378/98.8; 73/1.01, 1.86
See application file for complete search history.

(56) References Cited

U.S. PATENT DOCUMENTS

| | | | | |
|---|---|---|---|---|
| 4,300,046 A * | 11/1981 | Wang | ........................... | 378/62 |
| 5,829,444 A | 11/1998 | Ferre et al. | .................. | 128/897 |
| 6,120,180 A * | 9/2000 | Graumann | ................... | 378/206 |
| 6,484,049 B1 | 11/2002 | Seeley et al. | ................ | 600/426 |
| 6,490,475 B1 | 12/2002 | Seeley et al. | ................ | 600/426 |
| 6,636,757 B1 | 10/2003 | Jascob et al. | ................ | 600/424 |
| 6,776,526 B2 | 8/2004 | Zeiss | ........................... | 378/207 |
| 7,125,165 B2 * | 10/2006 | Lutjens et al. | .............. | 378/205 |
| 7,344,307 B2 | 3/2008 | Yatsenko et al. | ............ | 378/207 |
| 7,497,621 B2 | 3/2009 | Yatsenko et al. | ............ | 378/207 |
| 7,532,997 B2 | 5/2009 | Li et al. | ....................... | 702/150 |
| 2001/0036245 A1 * | 11/2001 | Kienzle et al. | .................. | 378/4 |
| 2004/0008809 A1 * | 1/2004 | Webber | ........................ | 378/8 |
| 2004/0076259 A1 * | 4/2004 | Jensen et al. | .................. | 378/91 |
| 2004/0258210 A1 * | 12/2004 | Ritter | ........................ | 378/198 |
| 2005/0107687 A1 * | 5/2005 | Anderson | ................... | 600/424 |
| 2006/0122495 A1 * | 6/2006 | Kienzle | ........................ | 600/424 |
| 2008/0172069 A1 * | 7/2008 | Dukesherer et al. | ......... | 606/130 |

* cited by examiner

*Primary Examiner*—Hezron Williams
*Assistant Examiner*—Tamiko D Bellamy
(74) *Attorney, Agent, or Firm*—McAndrews, Held & Malloy, Ltd.; Peter J. Vogel; Michael A. Dellapenna (57) ABSTRACT

Certain embodiments of the present invention provide methods and systems for imaging system calibration using a field replaceable unit. Certain embodiments provide a field replaceable unit for imaging system calibration. The unit includes an array of radio opaque fiducials arranged for use in image calibration for an imaging system. The unit also includes a plurality of receivers positioned around a periphery of a detector in the imaging system for use in navigation calibration for the imaging system. The unit further includes a connection for providing data regarding image calibration and navigation calibration to a processor. Additionally, the unit includes a frame for positioning the array of radio opaque fiducials and the plurality of receivers embedded in a concave target with respect to a detector in the imaging system.

20 Claims, 6 Drawing Sheets

SYSTEMS AND METHODS FOR INTEGRATING A NAVIGATION FIELD REPLACEABLE UNIT INTO A FLUOROSCOPY SYSTEM

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to imaging and image-guided navigation. In particular, the present invention relates to a system and method for improved calibration of equipment used in imaging and image-guided operations.

Medical practitioners, such as doctors, surgeons, and other medical professionals, often rely upon technology when performing a medical procedure, such as image-guided surgery or examination. A tracking system may provide positioning information for the medical instrument with respect to the patient or a reference coordinate system, for example. A medical practitioner may refer to the tracking system to ascertain the position of the medical instrument when the instrument is not within the practitioner's line of sight. A tracking system may also aid in pre-surgical planning.

The tracking or navigation system allows the medical practitioner to visualize the patient's anatomy and track the position and orientation of the instrument. The medical practitioner may use the tracking system to determine when the instrument is positioned in a desired location. The medical practitioner may locate and operate on a desired or injured area while avoiding other structures. Increased precision in locating medical instruments within a patient may provide for a less invasive medical procedure by facilitating improved control over smaller instruments having less impact on the patient. Improved control and precision with smaller, more refined instruments may also reduce risks associated with more invasive procedures such as open surgery.

Tracking systems may be ultrasound, inertial position, optical, or electromagnetic tracking systems, for example. Electromagnetic tracking systems may employ coils as receivers and transmitters. Typically, an electromagnetic tracking system is configured in an industry-standard coil architecture (ISCA). ISCA uses three colocated orthogonal quasi-dipole transmitter coils and three colocated quasi-dipole receiver coils. Other systems may use three large, non-dipole, non-colocated transmitter coils with three colocated quasi-dipole receiver coils. Another tracking system architecture uses an array of six or more transmitter coils spread out in space and one or more quasi-dipole receiver coils. Alternatively, a single quasi-dipole transmitter coil may be used with an array of six or more receivers spread out in space.

The ISCA tracker architecture uses a three-axis dipole coil transmitter and a three-axis dipole coil receiver. Each three-axis transmitter or receiver is built so that the three coils exhibit the same effective area, are oriented orthogonally to one another, and are centered at the same point. If the coils are small enough compared to a distance between the transmitter and receiver, then the coil may exhibit dipole behavior. Magnetic fields generated by the trio of transmitter coils may be detected by the trio of receiver coils. Using three approximately concentrically positioned transmitter coils and three approximately concentrically positioned receiver coils, for example, nine parameter measurements may be obtained. From the nine parameter measurements and one known position or orientation parameter, a position and orientation calculation may determine position and orientation information for each of the transmitter coils with respect to the receiver coil trio with three degrees of freedom.

In medical and surgical imaging, such as intraoperative or perioperative imaging, images are formed of a region of a patient's body. The images are used to aid in an ongoing procedure with a surgical tool or instrument applied to the patient and tracked in relation to a reference coordinate system formed from the images. Image-guided surgery is of a special utility in surgical procedures such as brain surgery and arthroscopic procedures on the knee, wrist, shoulder or spine, as well as certain types of angiography, cardiac procedures, interventional radiology and biopsies in which x-ray images may be taken to display, correct the position of, or otherwise navigate a tool or instrument involved in the procedure.

Several areas of surgery involve very precise planning and control for placement of an elongated probe or other article in tissue or bone that is internal or difficult to view directly. In particular, for brain surgery, stereotactic frames that define an entry point, probe angle and probe depth are used to access a site in the brain, generally in conjunction with previously compiled three-dimensional diagnostic images, such as MRI, PET or CT scan images, which provide accurate tissue images. For placement of pedicle screws in the spine, where visual and fluoroscopic imaging directions may not capture an axial view to center a profile of an insertion path in bone, such systems have also been useful.

When used with existing CT, PET or MRI image sets, previously recorded diagnostic image sets define a three dimensional rectilinear coordinate system, either by virtue of their precision scan formation or by the spatial mathematics of their reconstruction algorithms. However, it may be desirable to correlate the available fluoroscopic views and anatomical features visible from the surface or in fluoroscopic images with features in the 3-D diagnostic images and with external coordinates of tools being employed. Correlation is often done by providing implanted fiducials and adding externally visible or trackable markers that may be imaged. Using a keyboard or mouse, fiducials may be identified in the various images. Thus, common sets of coordinate registration points may be identified in the different images. The common sets of coordinate registration points may also be trackable in an automated way by an external coordinate measurement device, such as a suitably programmed off-the-shelf optical tracking assembly. Instead of imageable fiducials, which may for example be imaged in both fluoroscopic and MRI or CT images, such systems may also operate to a large extent with simple optical tracking of the surgical tool and may employ an initialization protocol wherein a surgeon touches or points at a number of bony prominences or other recognizable anatomic features in order to define external coordinates in relation to a patient anatomy and to initiate software tracking of the anatomic features.

Generally, image-guided surgery systems operate with an image display which is positioned in a surgeon's field of view and which displays a few panels such as a selected MRI image and several x-ray or fluoroscopic views taken from different angles. Three-dimensional diagnostic images typically have a spatial resolution that is both rectilinear and accurate to within a very small tolerance, such as to within one millimeter or less. By contrast, fluoroscopic views may be distorted. The fluoroscopic views are shadowgraphic in that they represent the density of all tissue through which the conical x-ray beam has passed. In tool navigation systems, the display visible to the surgeon may show an image of a surgical tool, biopsy instrument, pedicle screw, probe or other device projected onto a fluoroscopic image, so that the surgeon may visualize the orientation of the surgical instrument in relation to the imaged patient anatomy. An appropriate reconstructed CT or MRI image, which may correspond to the tracked coordinates of the probe tip, may also be displayed.

Among the systems which have been proposed for effecting such displays, many rely on closely tracking the position and orientation of the surgical instrument in external coordinates. The various sets of coordinates may be defined by robotic mechanical links and encoders, or more usually, are defined by a fixed patient support, two or more receivers such as video cameras which may be fixed to the support, and a plurality of signaling elements attached to a guide or frame on the surgical instrument that enable the position and orientation of the tool with respect to the patient support and camera frame to be automatically determined by triangulation, so that various transformations between respective coordinates may be computed. Three-dimensional tracking systems employing two video cameras and a plurality of emitters or other position signaling elements have long been commercially available and are readily adapted to such operating room systems. Similar systems may also determine external position coordinates using commercially available acoustic ranging systems in which three or more acoustic emitters are actuated and their sounds detected at plural receivers to determine their relative distances from the detecting assemblies, and thus define by simple triangulation the position and orientation of the frames or supports on which the emitters are mounted. When tracked fiducials appear in the diagnostic images, it is possible to define a transformation between operating room coordinates and the coordinates of the image.

In general, the feasibility or utility of a system of this type depends on a number of factors such as cost, accuracy, dependability, ease of use, speed of operation and the like. Intraoperative x-ray images taken by C-arm fluoroscopes alone have both a high degree of distortion and a low degree of repeatability, due largely to deformations of the basic source and camera assembly, and to intrinsic variability of positioning and image distortion properties of the camera. In an intraoperative sterile field, such devices are typically draped, which may impair optical or acoustic signal paths of the signal elements they employ to track the patient, tool or camera.

More recently, a number of systems have been proposed in which the accuracy of the 3-D diagnostic data image sets is exploited to enhance accuracy of operating room images, by matching these 3-D images to patterns appearing in intraoperative fluoroscope images. These systems may use tracking and matching edge profiles of bones, morphologically deforming one image onto another to determine a coordinate transform, or other correlation process. The procedure of correlating the lesser quality and non-planar fluoroscopic images with planes in the 3-D image data sets may be time-consuming. In techniques that use fiducials or added markers, a surgeon may follow a lengthy initialization protocol or a slow and computationally intensive procedure to identify and correlate markers between various sets of images. All of these factors have affected the speed and utility of intraoperative image guidance or navigation systems.

Correlation of patient anatomy or intraoperative fluoroscopic images with precompiled 3-D diagnostic image data sets may also be complicated by intervening movement of the imaged structures, particularly soft tissue structures, between the times of original imaging and the intraoperative procedure. Thus, transformations between three or more coordinate systems for two sets of images and the physical coordinates in the operating room may involve a large number of registration points to provide an effective correlation. For spinal tracking to position pedicle screws, the tracking assembly may be initialized on ten or more points on a single vertebra to achieve suitable accuracy. In cases where a growing tumor or evolving condition actually changes the tissue dimension or position between imaging sessions, further confounding factors may appear.

When the purpose of image guided tracking is to define an operation on a rigid or bony structure near the surface, as is the case in placing pedicle screws in the spine, the registration may alternatively be effected without ongoing reference to tracking images, by using a computer modeling procedure in which a tool tip is touched to and initialized on each of several bony prominences to establish their coordinates and disposition, after which movement of the spine as a whole is modeled by optically initially registering and then tracking the tool in relation to the position of those prominences, while mechanically modeling a virtual representation of the spine with a tracking element or frame attached to the spine. Such a procedure dispenses with the time-consuming and computationally intensive correlation of different image sets from different sources, and, by substituting optical tracking of points, may eliminate or reduce the number of x-ray exposures used to effectively determine the tool position in relation to the patient anatomy with the reasonable degree of precision.

However, each of the foregoing approaches, correlating high quality image data sets with more distorted shadowgraphic projection images and using tracking data to show tool position, or fixing a finite set of points on a dynamic anatomical model on which extrinsically detected tool coordinates are superimposed, results in a process whereby machine calculations produce either a synthetic image or select an existing data base diagnostic plane to guide the surgeon in relation to current tool position. While various jigs and proprietary subassemblies have been devised to make each individual coordinate sensing or image handling system easier to use or reasonably reliable, the field remains unnecessarily complex. Not only do systems often use correlation of diverse sets of images and extensive point-by-point initialization of the operating, tracking and image space coordinates or features, but systems are subject to constraints due to the proprietary restrictions of diverse hardware manufacturers, the physical limitations imposed by tracking systems and the complex programming task of interfacing with many different image sources in addition to determining their scale, orientation, and relationship to other images and coordinates of the system.

Several proposals have been made that fluoroscope images be corrected to enhance their accuracy. This is a complex undertaking, since the nature of the fluoroscope's 3D to 2D projective imaging results in loss of a great deal of information in each shot, so the reverse transformation is highly underdetermined. Changes in imaging parameters due to camera and source position and orientation that occur with each shot further complicate the problem. This area has been addressed to some extent by one manufacturer which has provided a more rigid and isocentric C-arm structure. The added positional precision of that imaging system offers the prospect that, by taking a large set of fluoroscopic shots of an immobilized patient composed under determined conditions, one may be able to undertake some form of planar image reconstruction. However, this appears to be computationally very expensive, and the current state of the art suggests that while it may be possible to produce corrected fluoroscopic image data sets with somewhat less costly equipment than that used for conventional CT imaging, intra-operative fluoroscopic image guidance will continue to involve access to MRI, PET or CT data sets, and to rely on extensive surgical input and set-up for tracking systems that allow position or image correlations to be performed.

Thus, it remains highly desirable to utilize simple, low-dose and low cost fluoroscope images for surgical guidance, yet also to achieve enhanced accuracy for critical tool positioning.

Magnetic fields may affect x-rays and other image energy sources. Additionally, gravity may affect geometry of an x-ray system. Focal length and piercing point of x-rays may change depending upon the position of a C-arm or other mobile component of an imaging system. A difference between an imaging angle and an angle of the Earth's magnetic field may cause distortion that affects a resulting image. Additionally, an operator or patient may bump the C-arm or other component of an imaging system during operation or positioning, which may affect a resulting image. Thus, there is a need for improved calibration to reduce an effect of distortion on an image.

Registration is a process of correlating two coordinate systems, such as a patient image coordinate system and an electromagnetic tracking coordinate system. Several methods may be employed to register coordinates in imaging applications. "Known" or predefined objects are located in an image. A known object includes a sensor used by a tracking system. Once the sensor is located in the image, the sensor enables registration of the two coordinate systems.

U.S. Pat. No. 5,829,444 by Ferre et al., issued on Nov. 3, 1998, refers to a method of tracking and registration using a headset, for example. A patient wears a headset including radiopaque markers when scan images are recorded. Based on a predefined reference unit structure, the reference unit may then automatically locate portions of the reference unit on the scanned images, thereby identifying an orientation of the reference unit with respect to the scanned images. A field generator may be associated with the reference unit to generate a position characteristic field in an area. When a relative position of a field generator with respect to the reference unit is determined, the registration unit may then generate an appropriate mapping function. Tracked surfaces may then be located with respect to the stored images.

However, registration using a reference unit located on the patient and away from the fluoroscope camera introduces inaccuracies into coordinate registration due to distance between the reference unit and the fluoroscope. Additionally, the reference unit located on the patient is typically small or else the unit may interfere with image scanning. A smaller reference unit may produce less accurate positional measurements, and thus impact registration.

Typically, a reference frame used by a navigation system is registered to an anatomy prior to surgical navigation. Registration of the reference frame impacts accuracy of a navigated tool in relation to a displayed fluoroscopic image. Therefore, a system and method that improve registration of the reference frame would be highly desirable. Improved registration may help to decrease error between reference frames and improve navigated tracking accuracy.

Aspects of imaging system variability may be addressed using tracking elements in conjunction with a calibration fixture or correction assembly to provide fluoroscopic images of enhanced accuracy for tool navigation and workstation display. The calibration fixture and use of the calibration fixture in tracking are described in further detail in U.S. Pat. No. 6,484,049 by Seeley et al., issued on Nov. 19, 2002, and U.S. Pat. No. 6,490,475 by Seeley et al., issued on Dec. 3, 2002. A reference unit may also be used, as described in further detail in U.S. Pat. No. 5,829,444 by Ferre et al., issued on Nov. 3, 1998. Radiopaque calibration markers, such as ball bearings (BBs), are used to calibrate components in an imaging system.

Calibration fixtures or reference units may be used to reduce registration error for a registration or reference frame and improve accuracy in navigated tracking of an instrument. A reference frame may include a calibration fixture. The calibration fixture may be removably attached in a precise position with respect to the camera or to the patient. One or more tracking elements or markers may be included in the calibration fixture. A tracking element may be a point-origin defining tracking element that identifies spatial coordinates and/or orientation of the tracking element and, therefore, an object to which the tracking element is attached. Thus, a tracking element may with one or more measurements determine a position of markers in the calibration fixture and a position and orientation of the fixture itself or a surface to which the fixture is attached.

Current fixtures use radiopaque, discrete markers in radiolucent material. Thus, a need exists for improved calibration fixtures and calibration markers. Typically, an array of discrete, dark markers, such as ball bearings, is arranged in multiple planes for use in calibration. A calibration system watches for spikes and attenuations in a recorded curve to identify the ball bearings in the image.

Examples of calibration fixtures are described in U.S. Pat. No. 5,829,444, mentioned above, and a U.S. patent application entitled "Method and System for Improved Correction of Registration Error in a Fluoroscopic Image", by Douglas Johnson and Lewis Levine, filed on Jun. 2, 2004 (Ser. No. 10/859,767), which is herein incorporated by reference. However, use of BBs or other calibration markers in a fixture may impose distortion or artifacts in resulting images. Although some work has been done to remove such artifacts, some distortion still remains, and there is a need for an improved system and method for reducing artifacts introduced in an image by calibration markers. A system and method for improved calibration and distortion reduction would be highly desirable.

Generally, a goal of intrinsic geometry calibration is to determine a location of an x-ray focal spot in relation to an x-ray detector. On existing x-ray systems, such as fixed-room or mobile C-arms, the focal spot location may vary by 10 mm or more over the full range of motion of the C-arm structure. A source of this variation may be elastic deflection of the C-arm itself, bearing backlash, and other component motions. Knowing the precise location of the focal spot is important for 3D reconstruction and 2D navigation.

Fluoroscopy-based 3D imaging and 2D and/or 3D surgical navigation require accurate characterization of imaging parameters such as the camera focal length, piercing point, and optical distortion parameters, etc. Since C-arm devices are mobile imaging equipment, camera calibration is usually performed with every X-ray exposure to compensate for the mechanical deflection of C-arm for different clinical setups. Calibration is typically accomplished by deploying a calibration fixture between the X-ray detector and source that encloses an array of discrete, radiopaque markers such as ball bearings (BBs) arranged in three dimensional spaces. The physical presence of the radiopaque BBs produces shadows on the acquired fluoro-image for estimation of the camera parameters is undesirable for image quality.

Depending on the size and location of the BBs, possible consequences of introducing BBs to the imaging chain include loss of important anatomical features (e.g., 2D cardiovascular imaging), introduction of metal scattering artifacts (e.g., 3D imaging), and bad pixel identification (e.g., flat panel detector IQ).

As mentioned above, prior geometry calibration procedures use a calibration phantom, which typically is comprised of a number of discrete fiducials arranged in a three-dimensional pattern. One such phantom uses a series of BBs arranged in a helix around an x-ray transparent cylinder. In an offline calibration procedure, images of the phantom are acquired throughout the motion trajectory of the C-arm and the intrinsic geometry parameters are computed. These parameters are assumed to remain unchanged and are used for subsequent in vivo scans. Another method uses one or more planes of BBs or crosshairs affixed to the detector surface. This calibration phantom is used clinically. After an image of the anatomy is taken, the intrinsic parameters are calculated and the image artifacts from the fiducials are removed via image processing techniques.

Both of the methods described suffer from disadvantages. The helical phantom and offline procedure assumes that the parameters will remain unchanged. Wear and damage to the device may affect the accuracy of the stored parameters. Furthermore, there may be situations where the user unknowingly is flexing the C-arm by unintended collision with the operating table. The second method suffers from image degradation from the removal of the image artifacts. Also, the depth of the calibration phantom (e.g., 8-10 cm) compromises the usable patient volume between the x-ray source and detector.

Thus, systems and methods that provide intrinsic parameter calculation for a variety of images would be highly desirable. Systems and methods that minimize image degradation would also be highly desirable. Additionally, systems and methods that provide imaging system calibration or characterization without the introduction of markers would be highly desirable.

Current fluoroscopic image navigation systems, such as the system described in U.S. Pat. No. 6,490,475 includes a single EM (electromagnetic) receiver, a camera calibration target, and an EM shield. Such systems were mainly designed for image intensifier-based fluoroscopy systems and are primarily used for two-dimensional (2D) surgical applications.

Tracking accuracy, navigable range, and metal tolerance are three challenging and conflicting concerns to be addressed when designing an EM tracking system. For fluoroscope-based 2D image navigation applications, both tracking volume (e.g., transmitter to receiver distance) and metal distortion can be managed by users via adjustment of an image intensifier with a calibration target attachment (e.g., fiducial markers, EM receiver, and shield) closer to a patient anatomy where a transmitter is usually placed.

Figure 1:
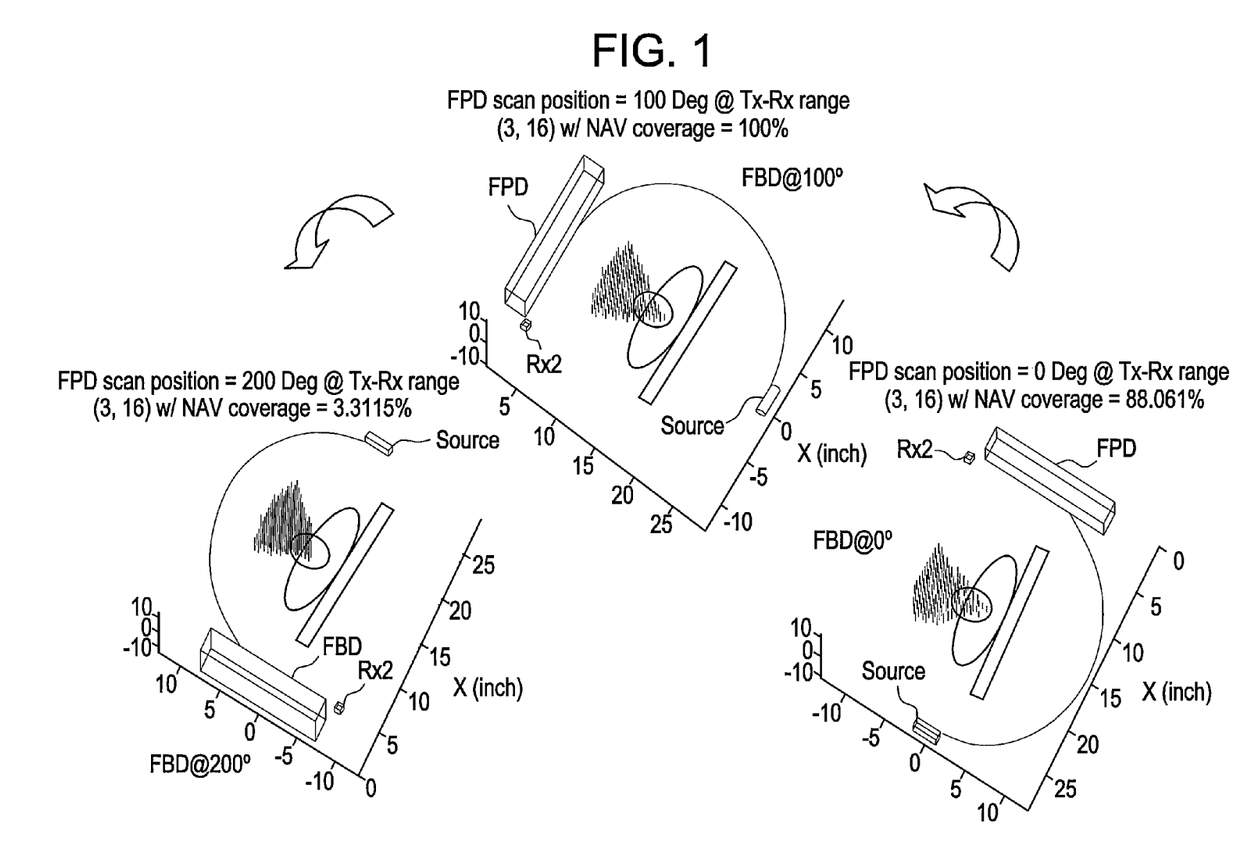
FIG. 1 illustrates a three dimensional sweep of a patient anatomy.
Figure 2:
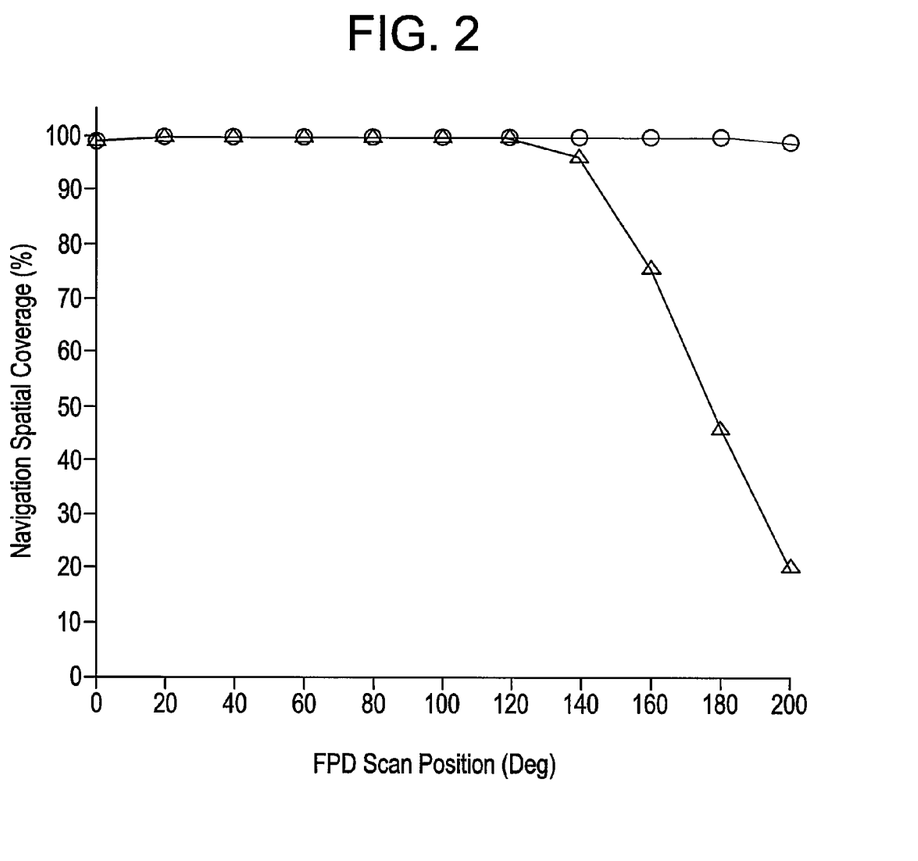
FIG. 2 illustrates a comparison of navigation coverage for a three dimensional C-arm sweep using single receiver and dual receiver navigation configurations.

For the 3D image navigation applications, however, the transmitter to calibration target receiver distance varies as the C-arm is rotated to different positions (See FIG. 1). Users generally have limited control of transmitter placements and depend on various clinical applications to fulfill a tracker range requirement. In a simulation study on the 3D sweeps of a typical thoracic spine using the present calibration target design, it has been shown that only 50% (for example, 20 to 120 degrees shown by the triangle solid line in FIG. 2) of 200 degree sweep positions have full navigation coverage of the prospective clinical volume.

Moreover, it also has been shown in FIG. 1 that a moving calibration target receiver may be positioned below the surgical table at a final position of a flat panel detector (FPD) sweep, which can cause tracker data loss due to the interference from the table.

Currently, a field replaceable unit (FRU) is implemented as a radio-translucent cylinder, such as a 3 inch tall plastic cylinder with an aluminum shield attachment. The height of the cylinder is primarily driven by design for reliable EM distortion mapping and accurate camera calibration. Specifically, in order to remove distortion from tracker measurements via a manufacturing robot mapping process, EM sensor placement is used to separate measurement from distorters (e.g., image intensifier, detector, shield, etc.) beyond a minimum separating distance found by experimental studies. Camera calibration design also requires a certain separating distance between fiducial layers along the direction of an X-ray projection in order to achieve a targeted accuracy.

However, when using an FPD with an iso-centric C-arm design, the effective C-arm object-to-imager distance (OID) may be reduce by about 20%. Such a reduction may not be acceptable for 2D cardiovascular or 3D imaging applications. Thus, an improved FRU design to compromise between navigation and imaging requirement is needed.

U.S. Pat. No. 6,636,757 relates to an EM navigation system including a transmitter array and shield used near a metal object, separate from a calibration target. U.S. Pat. No. 6,776,526 proposes a removal calibration target design for eliminating excessive occupation of the imaging space. The design of the calibration target is primarily based on integration of an optical navigation system. Thus, it does not address any EM related integration issues. U.S. Pat. No. 6,490,475 discloses a navigation target enclosing a single EM receiver, a multiple-layer radio opaque fiducials, and a shield. This target is designed and used for 2D spine or orthopedics image navigations.

Thus, there is a need for an FRU application to cardiovascular and 3D imaging applications. There is a need for systems and methods providing 3D navigation coverage with improved EM immunity to table and other interference, for example. There is a need for systems and methods to accommodate both 2D and 3D surgical navigation capabilities.

BRIEF SUMMARY OF THE INVENTION

Certain embodiments of the present invention provide methods and systems for imaging system calibration using a field replaceable unit.

Certain embodiments provide a field replaceable unit for imaging system calibration. The unit includes an array of radio opaque fiducials arranged for use in image calibration for an imaging system. The unit also includes a plurality of receivers positioned around a periphery of a detector in the imaging system for use in navigation calibration for the imaging system. The unit further includes a connection for providing data regarding image calibration and navigation calibration to a processor. Additionally, the unit includes a frame for positioning the array of radio opaque fiducials and the plurality of receivers with respect to a detector in the imaging system.

Certain embodiments provide a method for imaging system calibration. The method includes obtaining navigation information using a calibration target positioned with respect to a detector between an energy source and an image acquisition device in an imaging system. The calibration target includes a plurality of receivers providing navigation information. The method also includes determining a receiver coordinate system for the imaging system based on the navigation information. Additionally, the method includes obtaining image calibration data using an array of radio opaque fiducials arranged around a periphery of the detector between the image acquisition device and the energy source.

Certain embodiments provide a calibration target system for use in an imaging environment. The system includes a frame for positioning a plurality of components with respect to a detector mounted on a support member in an imaging environment. Further, the system includes an array of radio opaque fiducials mounted on the frame. The array of radio opaque fiducials is arranged to provide image calibration information. Additionally, the system includes a plurality of receivers positioned on the frame around a periphery of the detector to provide navigation information. The system also includes a shield arranged with respect to the frame to cover sides of the detector.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Certain embodiments provide a field replaceable unit (FRU) design that facilitates calibration capability for cardiovascular applications, 3D imaging applications, and 2D imaging examples, for example, including 3D navigation coverage, electromagnetic (EM) immunity to table interference, 3D imaging space conservation, etc. In certain embodiments, a mobile C-arm, L-arm, O-arm or similar device includes an integrated flat panel detector (FPD) and EM tracking system having both 2D and 3D surgical navigation capabilities. The FRU design has a dual EM receiver arrangement integrated with a bumper support. The system dynamically tracks and chooses tracker readings among a plurality of EM sensor outputs. The FRU envelope is concaved to match or closely approximate a C-arm object-to-imager distance (OID). Thus, the navigation FRU structure has a reduced impact on a 3D imaging space.

Figure 3:
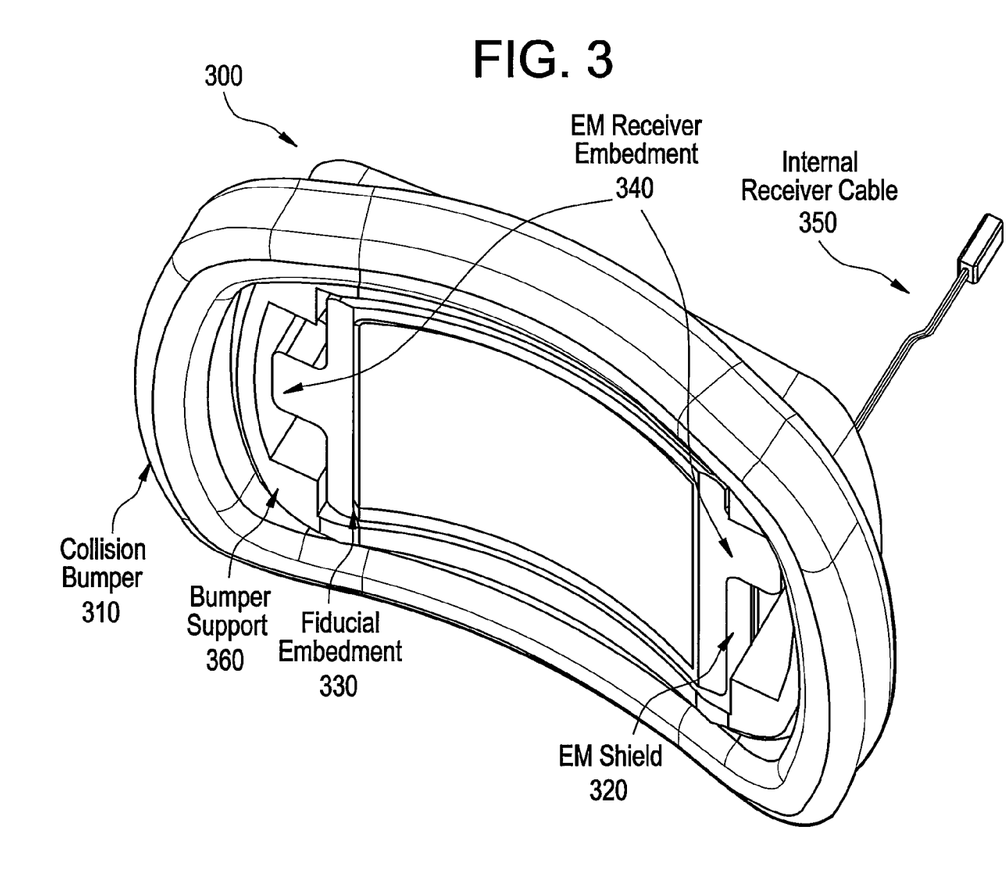
FIG. 3 illustrates a calibration target field replaceable unit in accordance with an embodiment of the present invention.

Certain embodiments provide an improved design for a navigation FRU. An exemplary embodiment of an FRU 300 is illustrated in FIG. 3. The navigation FRU 300 includes a collision bumper 310, an EM shield 320, an array of radio opaque fiducials 330, at least two EM receiver embedments 340, and a cable 350. The collision bumper 310 may be made from silicon and polycarbonate, for example. The shield 320 may be made from aluminum. The fiducials 330 may be made from stainless steel, for example. The cable 350 may include two sensor coils and wires, for example.

In the FRU 300, the two receiver packs 340 are integrated with a bumper support 360 (e.g., a plastic bumper support) and positioned with respect to front and back (e.g., close to the C-, L- or O-arm frame) peripheral sides of a detector, respectively. In certain embodiments, the receivers 340 are integrated with the bumper support 360 and positioned below a surface of the detector, such as approximately 40-mm below the surface of the detector. Positioning receivers 340 below a detector surface helps to increase navigation coverage for a 3D sweep in an orbital plane by managing a reduced number of receiver attachments. Receiver 340 positioning also helps to reduce or eliminate potential data loss due to surgical table interference with an EM tracker during an orbital sweep. For example, in certain embodiments, at least one receiver will be above the table during, for example, a 200-degree sweep.

In certain embodiments, each receiver pack 340 includes two identical or substantially identical three-coil sensors positioned a distance (e.g., roughly 40-mm) apart. In certain embodiments, one of the two sensors is used for navigation while the second sensor is used at least in part for hemisphere disambiguation and field integrity detection (FID), for example. The four EM sensors found in the receivers 340 each include an identifier, such as a programmable read-only memory identifier (PROM ID). The PROM ID is used to tag a signal data (e.g., mutual inductance) stream being received, as well as a distortion map installed on a processor communicating with the FRU 300. The processor determines a receiver coordinate system for transmitter position and orientation estimates (in the receiver coordinate system). For example, the receiver coordinate system is determined based on one or more quality metrics such as a shortest transmitter-to-receiver distance, a lowest FID number, etc. In accordance with another embodiment, the present technique provides a computer program, stored on a computer readable medium, for selecting an optimum receiver coordinate system to correct for one or more field distortions. The computer program is constructed and arranged to acquire signals representative of each of a plurality of EM sensors.

In certain embodiments, the cable 350 is an internal cable that is routed around the collision bumper frame 310. The cable 350 is routed around the bumper frame 310 starting from each receiver sensor and finishing on a connector drop to a tracker electronics board, for example, mounted on a C-arm.

In certain embodiments, the EM shield 320 is attached to the bumper frame 310. The shield 320 is designed to reduce variability of EM signatures between different C-arms so that the navigation installation is independent of a C-arm system configuration. In certain embodiments, the shield 320 is made from one or more thick conductive or ferromagnetic materials that largely attenuate distortion from the C-arm. In certain embodiments, the shield 320 is attached to the bumper 310 to cover four sides of the detector. The shield 320 may include flanges extending over the C-arm (or L-arm or O-arm, etc.) casting neck. The flanges further improve the shield effectiveness. The shield 320 design is also applicable to other positioners, such as L-arms, O-arms, etc.

The array of radio opaque fiducials 330 is arranged around the periphery of the detector between an image acquisition device and an X-ray source, for example. The fiducial array is rigidly attached to the bumper frame 310, for example. In certain embodiments, fiducial array depth is 40 mm. The fiducials may be clustered in the four corners of the window portion, for example.

To reduce or minimize FRU impact on a 3D imaging space, a "window" portion of the navigation FRU 300 (e.g., a side facing toward the X-ray source) is fabricated in a concave shape whose radius matches or approximates an OID (Object-to-Imager Distance) of the mobile C-arm. The navigation FRU 300 is attached to the mobile C-arm through a fastening mechanism on the casting neck of the C-arm. For example, clamps or screws may be used to attach the FRU 300 to the C-arm.

In certain embodiments, the dual receiver 340 arrangement helps to enable full navigation coverage of a prospective patient imaging space for 2D and 3D imaging. The dual receiver 340 arrangement also helps to eliminate potential data loss due to surgical table interference with an EM tracker. Concave FRU envelope design helps to reduce an impact on a 3D imaging space. A processor in communication with the FRU 300 helps to manage identification and output from multiple sensor embodiments in the FRU 300. In certain embodiments, the navigation FRU 300 is field replaceable and interchangeable between different C-arm, L-arm and O-arm systems.

Figure 4:
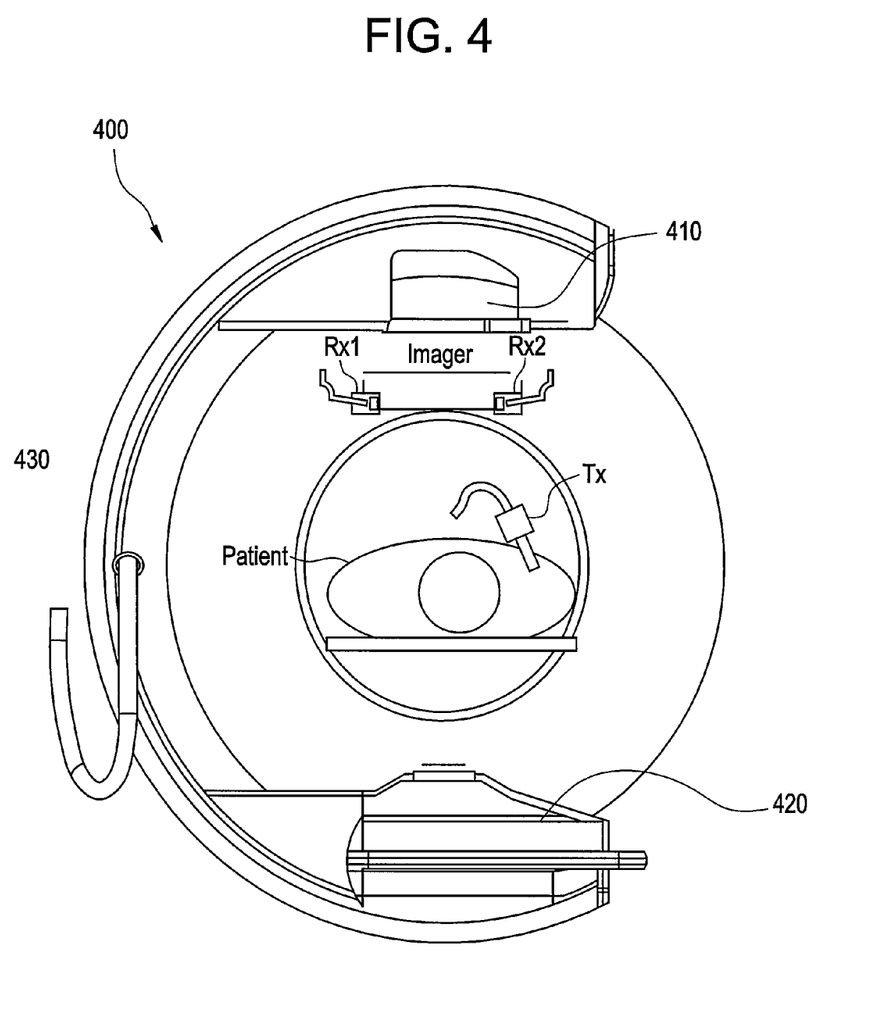
FIG. 4 illustrates an imaging system in accordance with an embodiment of the present invention.

The FRU 300 and other embodiments may be used in conjunction with a variety of imaging systems. As an example, FIG. 4 illustrates an imaging system 400 for use in an operating room environment. As shown in FIG. 4, the camera system 400 includes an imager 410, a camera source 420, a structural support member 430, sensors Rx1 and Rx2, and a transmitter Tx. The imager 410 may be an x-ray detector, for example. The camera source 420 may be an X-ray generator, for example. The structural support member 430 may be a C-arm, L-arm, O-arm and/or other structure supporting the imager 410 and source 420.

For example, the imager 410 may be mounted on the structural support member 36 opposite the camera source 420. The support member 430 moves about a patient or other object to produce two dimensional projection images of the patient from different angles. The patient or object remains positioned between the imager 410 and the source 420, and may, for example, be situated on a table or other support, although the patient/object may move.

Sensors Rx1 and Rx2 are positioned with respect to the camera source 420-. For example, the sensor Rx1 and Rx2 is affixed to or otherwise mounted on the source 420 Transmitter Tx is positioned with respect to an instrument, such as a probe or surgical tool, or with respect to a patient or other object. The instrument may be rigid, allowing the transmitter Tx to be fixed at a known or convenient position, such as on its handle. Alternatively, the tool may be a flexible tool, such as a catheter, flexible endoscope or an articulated tool, for example. In the latter cases, the transmitter Tx is preferably a small, localized element positioned in or at the operative tip of the tool to track coordinates of the tip within the body of the patient.

In an embodiment, the system 400, such as a fluoroscope system, operates with the imager 410 positioned opposite the X-ray source or generator 420. While in some systems, the imager 410 is fixed overhead and the source 420 is located below a patient support, the discussion below will be illustrated with regard to the more complex case of a typical C-arm fluoroscope, in which the imager or detector 410 and source 420 are connected by the structural support member 430, such as a C-arm, that allows movement of the imager 410 and camera source assembly 420 about the patient so that the C-arm may be positioned to produce x-ray views from different angles or perspectives. In such C-arm devices, the imaging beam generally diverges at an angle, the relative locations and orientations of the imager 410 and source 420 vary with position due to structural flexing and mechanical looseness, and the position of both the imager 410 and the source 420 with respect to the patient and/or a tool which it is desired to track may also vary in different shots.

Figure 5:
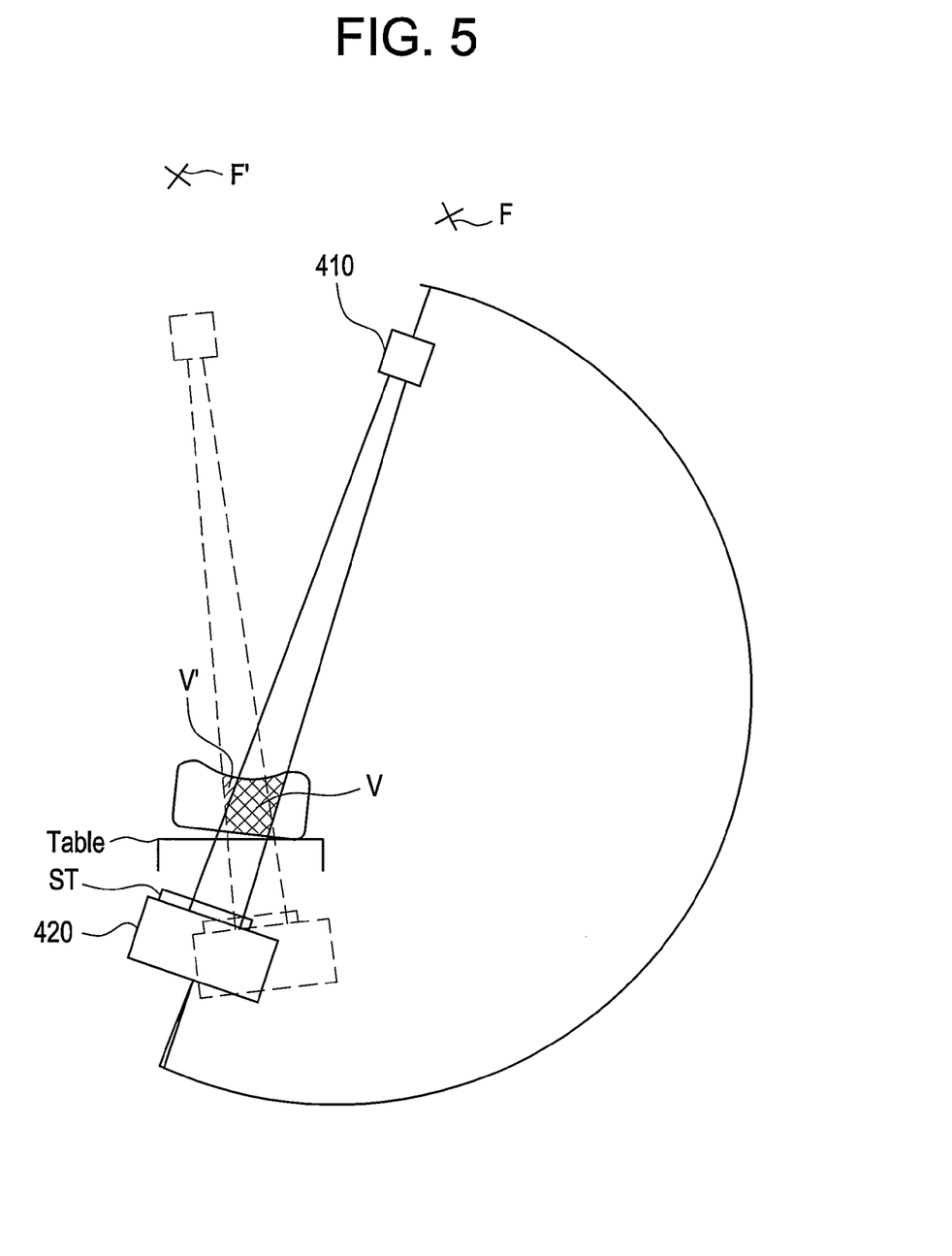
FIG. 5 illustrates a fluoroscope in two different imaging positions, with a first position shown in solid line, and a second position in dashed line phantom.

FIG. 5 illustrates the system 400 in two different imaging positions, with a first position shown in solid line, and a second position in dashed line phantom. In the first position, a tissue volume V is imaged with a divergent beam from the above right, and a virtual beam origin or focal point at F, while the image from the second position catches a largely overlapping but partly distinct tissue volume with a divergent beam from the upper left, and a different focal point F'. The distances from points F, F' to the camera may be different, and the camera itself may shift and tilt with respect to the beam and its center axis, respectively. In practice, the x-ray beam is generally aimed by its center ray, whose intersection with the imaging plane, referred to as the piercing point, may be visually estimated by aiming the assembly with a laser pointing beam affixed to the source. The x-ray beam may be considered to have a virtual origin or focal point F at the apex of the cone beam. Generally, the imager assembly 410 is positioned close to the patient, but may be subject to constraints posed by the operating table, the nature of the surgical approach, and tools, staging, clamps and the like, so that imaging of a tissue volume somewhat off the beam center line, and at different distances along the beam, may occur. As noted above, flexing of the C-arm or other support member 430 also changes the distance to the focal point F and this also may slightly vary the angular disposition of the beam to the camera source 420, so this shifting geometry may affect the fluoroscope images.

Furthermore, the camera source 420 may utilize an image sensing unit that itself introduces further distortions into the received distribution of image radiation. For example, the unit may involve a detector that employs a phosphor surface of generally curved contour to convert the x-ray image intensity distribution to a free electron distribution. Such a curved phosphor screen is generally placed over an electron multiplier or image intensifier assembly that provides an enhanced output video signal, but may further introduce a form of electron optical distortion that depends upon the intensifier geometry and varies with the orientation of the camera assembly in the earth's magnetic field. Other configurations of image detectors are also known or proposed, such as digital x-ray detectors or flat semiconductor arrays, which may have different imaging-end fidelity characteristics. Deflection or physical movement of the camera itself as well as electron/optical distortion from the camera geometry, image detector and variations due to gravitational, magnetic or electromagnetic fields may enter image reception and affect projective geometry and other distortion of a final image produced by the assembly.

Calibration of camera intrinsic parameters (e.g., focal length and image plane with respect to camera coordinate) corresponds to finding a transformation from an imager space to a camera space. The origin of the camera coordinate system is usually defined at the center of the camera source.

Figure 6:
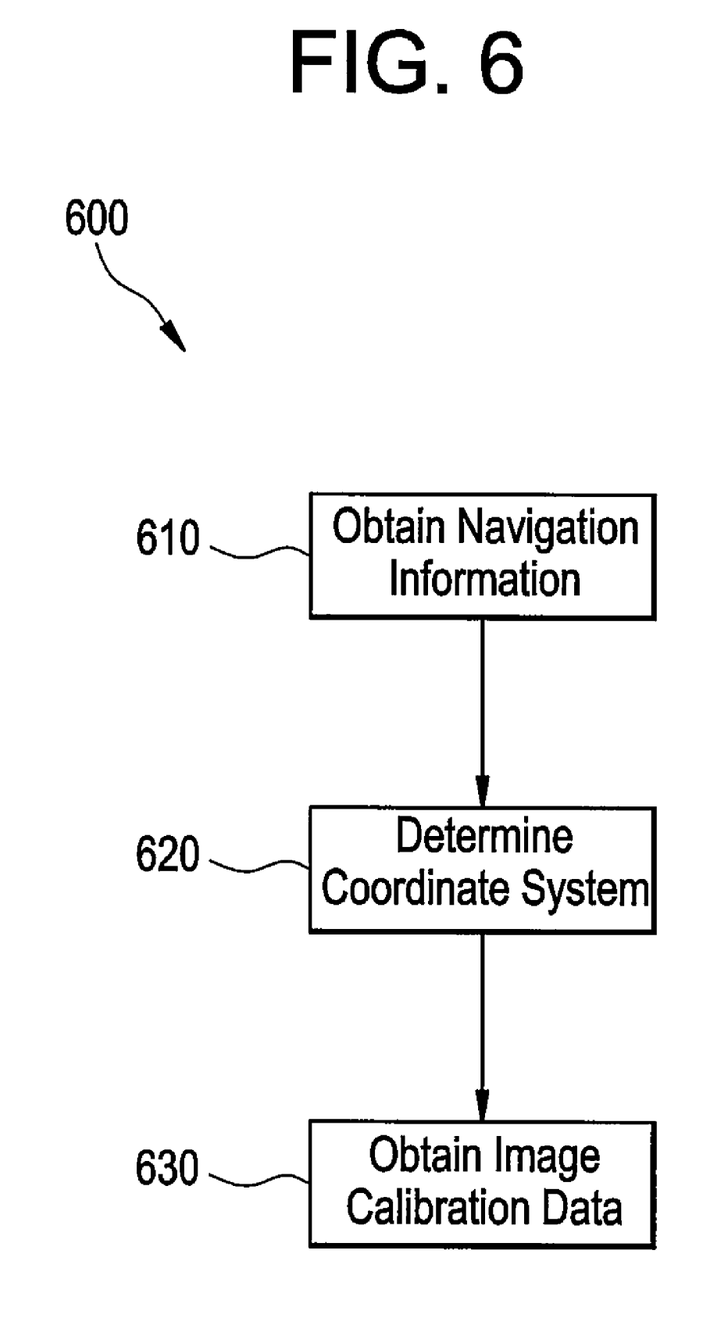
FIG. 6 illustrates a flow diagram for a method for imaging system calibration in accordance with an embodiment of the present invention.

FIG. 6 illustrates a flow diagram for a method 600 for imaging system calibration in accordance with an embodiment of the present invention. At step 610, navigation information, such as electromagnetic (EM) tracking information, is obtained using a calibration target, such as an FRU, positioned with respect to a detector. The detector is positioned between an image acquisition device and an energy source, such as an X-ray source. In certain embodiments, a shield is used to help reduce variability of EM signatures between different imaging systems. Tracking information is obtained, for example, using sensor pairs positioned around a periphery of the detector. In certain embodiments, one sensor in a sensor pair provides navigation information while the second sensor in the pair is used for hemisphere disambiguation and field integrity detection, for example. Navigation data from the sensors is associated with an identifier and passed to processing software and/or hardware, for example. Data may be passed via wired and/or wireless connection, for example.

At step 620, a receiver coordinate system is determined based on navigation information, such as position and orientation information. For example, the receiver coordinate system is determined based on a shortest transmitter to receiver distance and/or a lowest FID number.

For example, a transmitter-to-receiver distance of greater than eighteen inches (approx. 500 mm) may yield unreliable data for certain implementations with existing technologies. As such, if the transmitter-to-receiver distance increases, for example, due to movement of the C-arm, a reliable position and orientation for the C-arm may not be obtained. Without a reliable position and orientation for the C-arm, device position and orientation may not be accurately projected onto the diagnostic image.

Accordingly, a tracking system utilizing multiple EM receivers fixed in relation to the imaging system may be used to account for some of these complicating factors. For example, uncompensated distortions may not impact all of the EM receivers in the same manner so that one or more of the receivers may return acceptable data even where one of the receivers does not. Alternatively, dependent upon the position of the C-arm, one of the EM receivers may have an acceptable transmitter-to-receiver distance even if the other receiver does not.

At step 630, image calibration data is obtained using an array of radio opaque fiducials arranged around the periphery of the detector between the image acquisition device and the energy source. In certain embodiments, the surface on which the radio opaque fiducials are implemented is concave with a radius approximating an object-to-imager distance in the imaging system. In certain embodiments, the concave port faces the energy source (e.g., an X-ray energy source).

Thus, certain embodiments provide EM distortion mapping and accurate camera calibration in an imaging system, such as a mobile C-arm imaging system.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A field replaceable unit for imaging system calibration, said unit comprising:
an array of radio opaque fiducials arranged for use in image calibration for an imaging system;
a plurality of receivers positioned around a periphery of a detector in said imaging system for use in navigation calibration for the imaging system;
a connection for providing data regarding image calibration and navigation calibration to a processor; and
a frame for positioning said array of radio opaque fiducials and said plurality of receivers with respect to a detector in the imaging system.

2. The unit of claim 1, wherein each of said plurality of receivers comprises first and second sensors.

3. The unit of claim 2, wherein, in a sensor pair, said first sensor provides navigation information and said second sensor provides at least one of hemisphere disambiguation and field integrity detection.

4. The unit of claim 1, further comprising a bumper surrounding said array of radio opaque fiducials and said plurality of receivers.

5. The unit of claim 1, wherein the detector is mounted on a support member.

6. The unit of claim 5, wherein said support member comprises at least one of a C-arm, an L-arm and an O-arm.

7. The unit of claim 1, wherein said unit is configured for use with a plurality of imaging systems.

8. The unit of claim 1, further comprising a shield arranged to reduce variability of electromagnetic signatures between different imaging systems.

9. The unit of claim 1, wherein said unit includes a window portion and said window portion having a concave shape facing an energy source of the imaging system, said concave shape having a radius corresponding to an object-to-imager distance of the imaging system.

10. The unit of claim 1, further comprising a processor configured to determine a receiver coordinate system for the imaging system based on navigation data from said plurality of receivers.

11. The unit of claim 10, wherein said processor determines said receiver coordinate system based on at least one of a transmitter to receiver distance and a field integrity detection number.

12. A method for imaging system calibration, said method comprising:
obtaining navigation information using a calibration target positioned with respect to a detector between an energy source and an image acquisition device in an imaging system, said calibration target including a plurality of receivers providing navigation information;
determining a receiver coordinate system for the imaging system based on said navigation information; and
obtaining image calibration data using an array of radio opaque fiducials arranged around a periphery of the detector between the image acquisition device and the energy source.

13. The method of claim 12, further comprising calibrating the imaging system based on the receiver coordinate system and the image calibration data.

14. The method of claim 12, the receiver coordinate system is determined based on at least one of a transmitter to receiver distance and a field integrity detection number.

15. The method of claim 12, wherein each of said plurality of receivers includes a sensor pair providing navigation information and at least one of hemisphere disambiguation and field integrity detection.

16. The method of claim 12, further comprising tagging signal data from each of said plurality of receivers with an identifier for use in constructing a distortion map.

17. A calibration target system for use in an imaging environment, said system comprising:
a frame for positioning a plurality of components with respect to a detector mounted on a support member in an imaging environment;
an array of radio opaque fiducials mounted on said frame, said array of radio opaque fiducials arranged to provide image calibration information;
a plurality of receivers positioned on said frame around a periphery of the detector to provide navigation information; and
a shield arranged with respect to said frame to cover sides of the detector.

18. The system of claim 17, wherein said plurality of receivers are integrated with a bumper positioned to the front and back of the detector.

19. The system of claim 17, wherein each of said plurality of receivers includes two three-coil sensors.

20. The system of claim 19, wherein one of said two three-coil sensors provide navigation information and one of said two three-coil sensors provides at least one of hemisphere disambiguation and field integrity detection information.

* * * * *

UNITED STATES PATENT AND TRADEMARK OFFICE
CERTIFICATE OF CORRECTION

PATENT NO. : 7,621,169 B2
APPLICATION NO. : 11/553291
DATED : November 24, 2009
INVENTOR(S) : Li et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 458 days.

Signed and Sealed this

Twenty-sixth Day of October, 2010

David J. Kappos
*Director of the United States Patent and Trademark Office*